Figure 1:
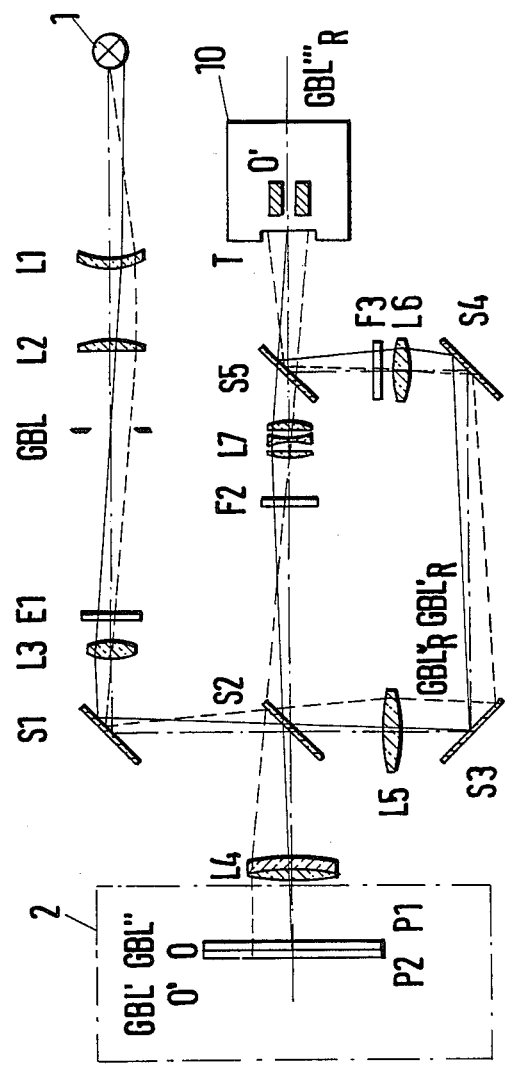

United States Patent [19]

Käser

[11] Patent Number: 4,842,407
[45] Date of Patent: Jun. 27, 1989

[54] APPARATUS FOR IMAGING AN OBJECT ON AN ELECTROOPTICAL TRANSDUCER

[75] Inventor: Manfred Käser, Friesenried, Fed. Rep. of Germany

[73] Assignee: J. Hirschmann Geratebau GmbH & Co. KG, Fed. Rep. of Germany

[21] Appl. No.: 67,097

[22] Filed: Jun. 26, 1987

[30] Foreign Application Priority Data

Jun. 27, 1986 [DE] Fed. Rep. of Germany ....... 3621631

[51] Int. Cl.$^4$ ............................................. G01N 27/26
[52] U.S. Cl. .................................... 356/344; 356/239
[58] Field of Search ............... 356/341, 344, 359, 360, 356/239; 358/107

[56] References Cited

U.S. PATENT DOCUMENTS

| 3,381,134 | 4/1968 | Wolf | 356/361 X |
|---|---|---|---|
| 3,623,812 | 11/1971 | Hannig et al. | 356/344 |
| 3,732,014 | 5/1973 | Uzgiris | 356/344 X |
| 4,191,476 | 3/1980 | Pollard | 356/360 X |

Primary Examiner—Davis L. Willis
Assistant Examiner—Matthew W. Koren
Attorney, Agent, or Firm—Ostrolenk, Faber, Gerb & Soffen

[57] ABSTRACT

An apparatus for imaging an object on an electrooptical transducer for measuring the transparency and/or the light dispersion of the object comprises a light source, a first beam path for illuminating the object and a second beam path for imaging the object on the electrooptical transducer. Furthermore, a third beam path is provided which forms a reference beam path and which conducts part of the light of the first beam path onto the same electrooptical transducer.

20 Claims, 2 Drawing Sheets

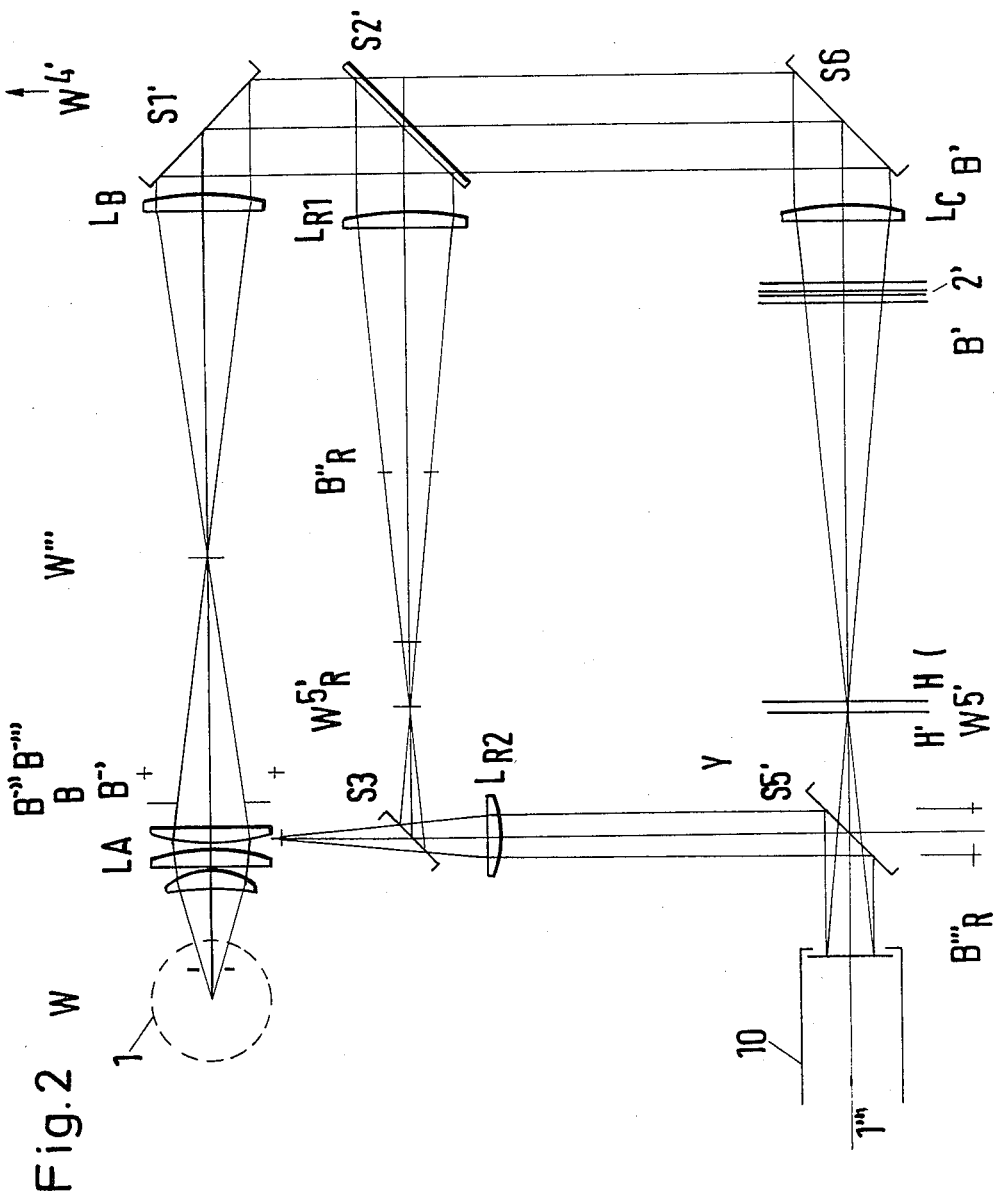

APPARATUS FOR IMAGING AN OBJECT ON AN ELECTROOPTICAL TRANSDUCER

The invention relates to an apparatus for imaging an object on an electrooptical transducer for measuring the transparency and/or dispersion of the object, comprising a light source, a first beam path for illuminating the object and a second beam path for imaging the object on the electrooptical transducer.

Such an apparatus can be used for example in electrophoresis techniques in which the object is disposed in an electrophoresis chamber which is formed by two glass plates arranged spaced apart from each other.

A problem in such apparatuses for imaging an object on an electrooptical transducer resides firstly in that the space required by the total beam path is to be kept as small as possible and that changes in the light power of the light source must not lead to measurement errors.

The reduction of the beam path represents in many cases a particular problem because the light incident on the object and the light conducted from said object onto the electrooptical transducer should impinge as perpendicularly as possible on the object because otherwise uncontrolled diffraction and dispersion effects are caused. This is in particular the case when the object to be imaged is sheetform as is the case for example with electrophoresis objects. The reduction of the space requirement is further made difficult by the need for additional transducers for controlling the light output of the light source, which measure said output and permit compensation of light output changes.

The invention is based on the problem of providing an apparatus of the type mentioned at the beginning which with small space requirement permits perpendicular impinging of the light from the first ray path on the object and with which changes of the light power do not result in any measurement errors.

This problem is solved by the features set forth in the characterizing clause of claim 1.

Advantageous further developments and embodiments of the invention are set forth in the subsidiary claims.

With the configuration of the apparatus according to the invention a part of the light coming from the light source is always conducted in the first ray path via the reference ray path to the same electrooptical transducer on which the image of the object from the second ray path is also formed so that a compensation of changes of the light power of the light source can be carried out properly without a second transducer being required to check the light power. Furthermore, changes of the light power are also corrected within the first beam path itself.

According to a further development of the invention the reference beam path conducts the light of the first beam path to the transducer locally offset so that a comparison of the measuring image with the reference image is continuously possible.

According to a further development of the invention the reference beam path conducts the light of the first beam path offset in time to the transducer so that alternately with the measurement of the measuring image the measurement of the reference image can take place.

According to a further advantageous development of the invention the first beam path and the reference beam path are bent several times so that in spite of using the reference beam path small dimensions of the apparatus are achieved.

According to a further development of the invention in which the object is illuminated with incident light on the side of the object remote from the first beam path a mirror is disposed and the light of the light source is deflected via a first 45-degree mirror through 90 degrees and impinges on a semireflecting mirror which introduces a part of the light of the first beam path into the reference beam path and on the other hand illuminates the object. The light reflected back from the mirror onto the rear side of the object is introduced via the semireflecting mirror without change of direction into the second beam path, the direction of which is opposite to the direction of the first beam path prior to the first deflection mirror. The reference beam path includes two further 45-degree mirrors which reflect the light into the second beam path via a semireflecting mirror.

In a further embodiment of the invention operating with transmitted light the first beam path also contains a first 45-degree deflection mirror and a second 45-degree deflection mirror between which a semireflecting mirror is disposed which introduces part of the light into the reference beam path. From the second deflection mirror the light goes to the object and passes through the latter without changing direction to the second beam path in which a semireflecting mirror is also disposed which serves to reflect in the light of the reference beam path which includes a further deflection mirror which receives the light from the semireflecting mirror in the first beam path. In this case as well the direction of the light in the second beam path is opposite to the direction of the first beam path, the reference beam path also accordingly having a portion in which the light extends in the opposite direction to the first beam path so that small length dimensions of the combination of the beam paths results.

Embodiments of the invention will be explained hereinafter with reference to their use in an electrophoresis apparatus and with the aid of the drawings, wherein:

FIG. 1 shows a first embodiment of the electrophoresis apparatus for incident light illumination, FIG. 2 shows an embodiment of the electrophoresis apparatus for transmitted light illumination.

In the embodiment illustrated in FIG. 1 the object is formed by an electrophoresis chamber 2 which comprises a glass plate P1 and a glass plate P2 metallized at its rear surface, the actual electrophoresis object being disposed between these glass plates and effecting a light dispersion or light absorption.

A light source 1 cooperates with a first beam path comprising condenser lenses L1, L2 and a field-of-view diaphragm GBL, a further lens L3, a first 45-degree mirror S1 and a semireflecting deflection mirror S2. The mirror S1 disposed at 45 degrees deflects the light through 90 degrees from the first direction between the light source 1 and the mirror S1, part of said light passing through the semireflecting mirror and being introduced via a lens L5 into a reference beam path. The other part of the light is again deflected through 90 degrees so that it runs again in the first direction and via a lens L4 reaches the electrophoresis chamber. The image of the electrophoresis object reflected back at the rear side of the metallized glass plate again passes through the lens L4 and the semireflecting mirror S2 without change of direction and via an objective L7 and a nonmetallized region of a 45-degree mirror S5 impinges on the target face of the electrooptical transducer 10 which can be formed by a television camera.

The reference beam path contains a first and a second 45-degree deflection mirror S3, S4 between which the light coming from the lens L5 runs in the direction opposite to the first direction, the light coming from the second deflection mirror being incident via a lens 6 on the metallized region of the mirror S5 which conducts said light likewise to the target face of the electrooptical transducer 10, preferably offset with respect to the image of the electrophoresis apparatus so that on said target face a measuring image and a reference image are available which can be compared with each other to compensate changes of the light power of the light source 1 or losses in the first beam path.

In the embodiment illustrated in FIG. 1 the image of the object and the image from the reference beam path are laterally inverted with respect to each other on the transducer 10. If this is undesirable a further reversing lens can for example be disposed between the mirrors S3 and S4, it being of course possible to arrange this lens at another point of the reference beam path or of the second beam path in order to eliminate the lateral inversion.

It is further possible to form the measuring image and the reference image consecutively in time, for example by a corresponding controllable shutter in the second beam path and the reference beam path, this possibly resulting in a simplification of the following evaluation devices of the electrooptical transducer 10.

With the embodiment described fluorescence measurements may also be carried out if the mirror S2 is constructed as colour divider, an excitation filter F1 being disposed in the first beam path and a barrier filter F2 in the second beam path.

In the second embodiment illustrated in FIG. 2 the first beam path includes, starting from the light source 1, a first lens arrangement LA and a second lens LB which conducts the light onto a first 45-degree mirror S1'. The latter mirror deflects the light through 90 degrees and conducts it via a semireflecting mirror S2' onto a second 45-degree mirror S6. The semireflecting mirror S2' reflects part of the light after changing the direction through 90 degrees into the reference beam path via a lens LR1.

The second deflection mirror S6 deflects the light into a direction which is opposite to the first direction in the first beam path between the light source and the first deflection mirror S1', said light passing through a lens LC and the electrophoresis chamber 2' which is formed in this case by two glass plates arranged spaced apart from each other. After passing through the electrophoresis chamber 2' the light of the first beam path enters the second beam path in which once again a semireflecting mirror S5' is disposed which serves to reflect the light of the reference beam path into the second beam path. Said reference beam path includes apart from the lens LR1 a further deflection mirror S3', the light between the lens LR1 and the deflection mirror S3' running in a direction opposite to the first direction. The mirror S3' conducts the light of the reference beam path through a lens SR2 onto the semireflecting mirror S5' into the second beam path.

In the two embodiments described in spite of the provision of a reference beam path a relatively compact arrangement of small overall length is obtained, both for transmitted light illumination and for incident light illumination.

I claim:

1. Apparatus for imaging an object on an electrooptical transducer for measuring the transparency and/or dispersion of the object, comprising a light source, a first beam path for illuminating the object and a second beam path for imaging the object on the electrooptical transducer, characterized in that a third beam path is provided which forms a reference beam path (S2, S3, S4, S5; S2', S3', S5') and which conducts a part of the light of the first beam path (L1, L2, L3, S1, S2, LA, LB, S1', S2', S5, LC) onto the same electrooptical transducer (10), and the reference beam path conducting the light of the first beam path to the transducer (10) locally offset with respect to the image of the object.

2. Apparatus according to claim 1, characterized in that the object is illuminated with incident light, that the first beam path (L1, L2, L3, S1, S2) comprises a 45-degree mirror (S1) on which the light of the light source (1) impinges in a first direction and a semireflecting 45-degree mirror (S2) which receives the light from the first mirror and conducts a part of said light onto the object (2) whilst the part of the light passing through the semireflecting mirror is introduced into the reference beam path.

3. Apparatus according to claim 1, comprising a semireflecting mirror (S2) which conducts the light of the first beam path onto the object, a mirror (P2) disposed behind the object (2) and which conducts the light passing though the object back to the semireflecting mirror (S2) and through the latter into the second beam path (L7, S5).

4. Apparatus according to claim 1, characterized in that the object (2) is illuminated with transmitted light, that the first beam path (S1', S2', S6', LC) comprises a first 45-degree deflection mirror (S1') on which the light from the light source (1) impinges in a first direction, a beam divider (S2') which conducts the light from the deflection mirror (S1') onto a second deflection mirror (S6) disposed in the first beam path without change of direction and onto a third deflection mirror (S3') arranged in the reference beam path in a direction opposite to the first direction, and that the light from the second deflection mirror (S6) is conducted through the object (2) into the second beam path (S5') in a direction opposite to the first direction.

5. Apparatus according to claim 4, characterized in that the third deflection mirror (S3') deflects the light of the reference beam path in a direction onto the second beam path which includes a semireflecting 45-degree mirror (S5') which conducts both the light from the object (2) and the light from the reference beam path onto the electrooptical transducer (10).

6. Apparatus according to claim 1, characterized in that the electrooptical transducer is a television camera.

7. Apparatus according to claim 1, characterized in that it is used to image an electrophoresis object on the electrooptical transducer (10).

8. Apparatus for imaging an object on an electrooptical transducer for measuring the transparency and/or dispersion of the object, comprising a light source, a first beam path for illuminating the object and a second beam path for imaging the object on the electrooptical transducer, characterized in that a third beam path is provided which forms a reference beam path (S2, S3, S4, S5; S2', S3', S5') and which conducts a part of the light of the first beam path (L1, L2, L3, S1, S2; LA, LB, S1', S2', S5, LC) onto the same electrooptical transducer (10), and the reference beam path conducting the light of the first beam path to the transducer (10) offset in time with respect to the light of the second beam path.

9. Apparatus according to claim 8 characterized in that the object is illuminated with incident light, that the first beam path (L1, L2, L3, S1, S2) comprises a 45-degree mirror (S1) on which the light of the light source (1) impinges in a first direction and a semireflecting 45-degree mirror (S2) which receives the light from the first mirror and conducts a part of said light onto the object (2) whilst the part of the light passing through the semireflecting mirror is introduced into the reference beam path.

10. Apparatus according to claim 8 further comprising a semireflecting mirror (S2) which conducts the light of the first beam path onto the object a mirror (P2) disposed behind the object (2) and which conducts the light passing through the object back to the semireflecting mirror (S2) and through the latter into the second beam path (L7, S5).

11. Apparatus according to claim 8 characterized in that the electrooptical transducer is a television camera.

12. Apparatus according to claim 8, characterized in that it is used to image an electrophoresis object on the electrooptical transducer (10).

13. Apparatus for imaging an object on an electrooptical transducer for measuring the transparency and/or dispersion of the object, comprising a light source, a first beam path for illuminating the object and a second beam path for imaging the object on the electrooptical transducer, a third beam path for forming a reference beam path (S2, S3, S4, S5; S', S3', S5') and which conducts a part of the light of the firstbeam path (L1, L2, L3, S1, S2; LA, LB, S1', S2', S5, LC) onto the same electrooptical transducer (10), a semireflecting mirror (S2) which conducts the light of the first beam path (S2) onto the object a mirror (P2) disposed behind the object (2) and which conducts the light passing through the object back to the semireflecting mirror (S2) and through the latter into the second beam path (L7, S5).

14. Electrophoresis apparatus according to claim 13, characterized in that the reference beam path comprises a first 45-degree deflection mirror (S3) which conducts the light derived from the semireflecting mirror (S2) on in a direction opposite to the first beam path, that the reference beam path comprises a second 45-degree deflection mirror (S4) which deflects the light from the first deflection mirror (S3) in the direction onto the second beam path and that in the region of the second beam path a further mirror (S5) is disposed which does not influence the light from the first semireflecting mirror (S2) and which deflects the light from the second deflection mirror (S4) onto the transducer (10).

15. Apparatus according to claim 13 characterized in that the object is illuminated with incident light, that the first beam path (L1, L2, L3, S1, S2) comprises a 45-degree mirror (S1) on which the light of the light source (1) impinges in a first direction and a semireflecting 45-degree mirror (S2) which receives the light from the first mirror and conducts a part of said light onto the object (2) whilst the part of the light passing through the semireflecting mirror is introduced into the reference beam path.

16. Apparatus for imaging an object on an electrooptical transducer for measuring the transparency and/or dispersion of the object, comprising a light source, a first beam path for illuminating the object and a second beam path for imaging the object on the electrooptical transducer, a third beam path which forms a reference beam path (S2, S3, S4, S5; S2', S3', S5') and which conducts a part of the light of the first beam path (L1, L2, L3, S1, S2; LA, LB, S1', S2', S5, LC) onto the same electrooptical transducer (10), that the object is illuminated with incident light, the first beam path (L1, L2, L3, S1, S2) comprises a first 45-degree mirror (S1) on which the light of the light source (1) impinges in a first direction and a second semireflecting 45-degree mirror (S2) which receives the light from the first mirror and conducts a part of said light onto the object (2) while the part of the light passing through the second semireflecting mirror is introduced into the reference beam path, the reference beam path comprises a third 45-degree deflection mirror (S3) which conducts the light derived from the second semireflecting mirror (S2) on in a direction opposite to the first beam path, the reference beam path comprises a fourth 45-degree deflection mirror (S4) which deflects the light from the third deflection mirror (S3) in the direction onto the second beam path and in the region of the second beam path a fifth mirror (S5) is disposed which does not influence the light from the second semireflecting mirror (S2) and which deflects the light from the fourth deflection mirror (S4) onto the transducer (10).

17. Apparatus according to claim 16 wherein the second semireflecting mirror (S2) conducts the light of the first beam path onto the object in a direction corresponding to the first direction, that behind the object (2) a sixth mirror (P2) is disposed which conducts the light passing through the object back to the second semireflecting mirror (S2) and through the latter into the second beam path (L7, S5).

18. Apparatus for imaging an object on an electrooptical transducer for measuring the transparency and/or dispersion of the object, comprising a light source, a first beam path for illuminating the object and a second beam path for imaging the object on the electrooptical transducer, characterized in that a third beam path is provided which forms a reference beam path (S2, S3, S4, S5; S2', S3', S5') and which conducts a part of the light of the first beam path (L1, L2, L3, S1, S2; LA, LB, S1', S2', S5, LC) onto the same electrooptical transducer (10), that the object (2) is illuminated with transmitted light, that the first beam path (S1', S2', S6', LC) comprises a first 45-degree deflection mirror (S1') on which the light from the light source (1) impinges in a first direction, a beam divider (S2') which conducts the light from the deflection mirror (S1') onto a second deflection mirror (S6) disposed in the first beam path without change of direction and onto a third deflection mirror (S3') arranged in the reference beam path in a direction opposite to the first direction, and that the light from the second deflection mirror (S6) is conducted through the object (2) into the second beam path (S5') in a direction opposite to the first direction.

19. Apparatus according to claim 18, characterized in that the third deflection mirror (S3') deflects the light of the reference beam path in a direction onto the second beam path which includes a semireflecting 45-degree mirror (S5') which conducts both the light from the object (2) and the light from the reference beam path onto the electrooptical transducer (10).

20. Apparatus for imaging an object on an electrooptical transducer for measuring the transparency and/or dispersion of the object, comprising a light source, a first beam path for illuminating the object and a second beam path for imaging the object on the electrooptical transducer, characterized in that a third beam path is provided which forms a reference beam path (S2, S3, S4, S5; S2', S3', S5') and which conducts a part of the light of the first beam path (L1, L2, L3, S1, S2; LA, LB, S1', S2', S5, LC) onto the same electrooptical transducer (10), said apparatus being used to image an electrophoresis object on the electrooptical transducer (10).

* * * * *